United States Patent

Sembritzki et al.

(10) Patent No.: US 6,272,199 B1
(45) Date of Patent: Aug. 7, 2001

(54) COMPUTER TOMOGRAPHY APPARATUS

(75) Inventors: Otto Sembritzki, Wachenroth; Heinrich Wallschlaeger, Erlangen, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/433,922

(22) Filed: Nov. 4, 1999

(30) Foreign Application Priority Data

Nov. 9, 1998 (DE) .............................................. 198 51 556

(51) Int. Cl.$^7$ ....................................................... A61B 6/03
(52) U.S. Cl. ................. 378/14; 378/11; 378/901
(58) Field of Search ................. 378/4, 11, 14, 378/15, 901

(56) References Cited

U.S. PATENT DOCUMENTS

| | | | |
|---|---|---|---|
| 4,008,400 | 2/1977 | Brunnett et al. | 378/4 |
| 4,637,040 | 1/1987 | Sohval et al. | 378/9 |
| 5,361,291 | * 11/1994 | Toth et al. | 378/12 |
| 5,430,785 | * 7/1995 | Pfoh et al. | 378/19 |
| 5,625,661 | * 4/1997 | Oikawa | 378/15 |
| 6,047,040 | * 4/2000 | Hu et al. | 378/19 |

* cited by examiner

Primary Examiner—David V. Bruce
(74) Attorney, Agent, or Firm—Schiff Hardin & Waite

(57) ABSTRACT

A CT apparatus with alternating focus, in which the detector elements deliver output data when picking up individual projections corresponding to the beam attenuation of the X-rays proceeding to the detector element, the number of data items correspond to twice the number of detector elements participating in the pick-up of each projection. The output data are converted into image reconstruction data, which contain a number of data items per projection which is greater than twice the number of detector elements participating in the pick-up of the respective projection.

6 Claims, 2 Drawing Sheets

COMPUTER TOMOGRAPHY APPARATUS

BACKGROUND OF THE INVENTION

1. Field of the Invention

The present invention relates to an X-ray computed tomography (CT) apparatus.

2. Description of the Prior Art

A CT apparatus is described in U.S. Pat. No. 4,637,040 which has an X-ray source which is rotated around an examination subject for obtaining datasets (projections) from a number of different projection angles, the X-ray source having a focus which is moved back and forth between two end positions (alternating focus). A detector system, composed of a number of detector elements, receives the X-rays emanating from the alternating focus and attenuated by the examination subject. Successive, adjacent detector elements which are disposed at a grid element spacing from an adjacent detector element, each detector element having an aperture. The detector elements in the aperture emit output data, corresponding to the aforementioned attenuated X-rays, the number of output data items corresponding to the number of detector elements which participate in obtaining the data for a given projection. The output data are supplied to a computer which reconstructs an image of the examination subject, or a portion thereof, based on the output data.

In a CT apparatus such as this, besides the size of the focus of the X-ray source, the MTF (Modulation Transfer Function) of the reconstruction algorithm and the pixel size of the reconstructed image, the scanning frequency with which the projection set is obtained, and thus the grid element spacing between immediately adjacent detector elements, are important determinants of the achievable spatial resolution.

The movement of the focus between two end positions, that is, the use of an X-ray tube with an alternating focus, serves to enhance the spatial resolution, by increasing the scanning frequency, and is taught by the above cited U.S. Pat. No. 4,637,040.

In addition, U.S. Pat. No. 4,008,400 to increase the scanning frequency by obtaining complementary projection datasets by what is known as the $\lambda/4$ shift. However, the $\lambda/4$ shift presumes a CT-device with highly stable and precise mechanical relations and is also not very effective when the path radius at which the focus of the X-ray source moves around the subject is short.

SUMMARY OF THE INVENTION

An object of the present invention is to provide a CT apparatus of the above type wherein it is possible to enhance the spatial resolution even given a short path radius of the focus of the X-ray source, without placing higher requirements on the mechanical stability of the CT apparatus.

This object is inventively achieved in a CT-device having an X-ray source which is moved around a subject for irradiating a subject from a number of projection angles, and a detector system for receiving the radiation emanating from the focus. The focus is moved back and forth between two end positions in the X-radiation source. The detector elements of the detector system are arranged in succession, each detector element being spaced from an adjacent detector element by a grid element spacing and each detector element having an aperture. The data represent the beam attenuation in the path of the X-rays to the respective detector element. The number of data items is twice the number of detector elements participating in capturing the projection. An electronic computing unit converts the output data into image reconstruction data. These data contain a number of data items per projection which is greater than twice the number of detector elements participating in the pick-up of the respective projection, preferably by a factor that is at least equal the ratio of the grid element spacing to the aperture size. The electronic computing unit reconstructs an image based on the image reconstruction data.

The invention makes use of the fact that the maximum spatial frequency that is contained in the output data corresponds to the detector aperture. This information is obtained but unused in conventional CT devices, since, due to the movement of the focus between two end positions, the number of output data items per projection corresponds to twice the number of detector elements participating in picking up the projection, and so the maximum spatial frequency corresponds to the grid element spacing. In the case of the invention, however, a conversion of the output data into image reconstruction data takes place, so that the maximum spatial frequency contained in the output data is used.

It is well known that in practice the maximum achievable spatial resolution usually does not reach the zero position that is predetermined by the aperture. Rather, 95% of the theoretical maximum can be expected in practice.

In a preferred embodiment of the invention, the output data represent fan projections, while the image reconstruction data represent parallel projections. The enhancement of the spatial resolution occurs in the course of the conversion of the output data representing the fan projections into data representing parallel projections, which serve for image reconstruction, this conversion preferably occurring by interpolation. This corresponds to the conversion into a new coordinate system by linking location information, that is, output data that have been collected in the capturing of various fan projections. In a further embodiment of the invention, in the interpolation signal portions with a spatial frequency greater than or equal to the reciprocal of the grid element spacing of the detector are substantially suppressed. One suitable interpolation function is described by the equation:

$$h_1{}^a(\beta,\Delta\beta)=ch_1(\beta,\Delta\beta)+(1-c)h_1{}'(\beta,\Delta\beta) \tag{1}$$

wherein $h_1$ is the interpolation kernel of the linear interpolation, for which the following equation applies:

$$h_1(\beta, \Delta\beta) = \begin{cases} 1 - \dfrac{|\beta|}{\Delta\beta} & |\beta| \leq \Delta\beta \\ 0 & \Delta\beta < |\beta| \end{cases} \text{ for} \tag{2}$$

wherein $h^r_1$ is defined by $$h^r_1(\beta, \Delta\beta) = \tag{3}$$

$$\begin{cases} \dfrac{1}{3}\left(1 + \sqrt{1 - 3\left(\dfrac{\beta}{\Delta\beta}\right)^2}\right) & |\beta| \leq 0.5\Delta\beta \\ \dfrac{1}{6}\left(2 + 3\left(1 - \left|\dfrac{\beta}{\Delta\beta}\right|\right) - \sqrt{1 - 3\left(1 - \left|\dfrac{\beta}{\Delta\beta}\right|\right)^2}\right) & \text{for } 0.5\Delta\beta < |\beta| \leq 1.5\Delta\beta \\ 0 & 1.5\Delta\beta < |\beta| \end{cases}$$

and wherein $\beta$ is the fan channel angle and $\Delta\beta$ is its increment.

DESCRIPTION OF THE PREFERRED EMBODIMENTS

Figure 1:
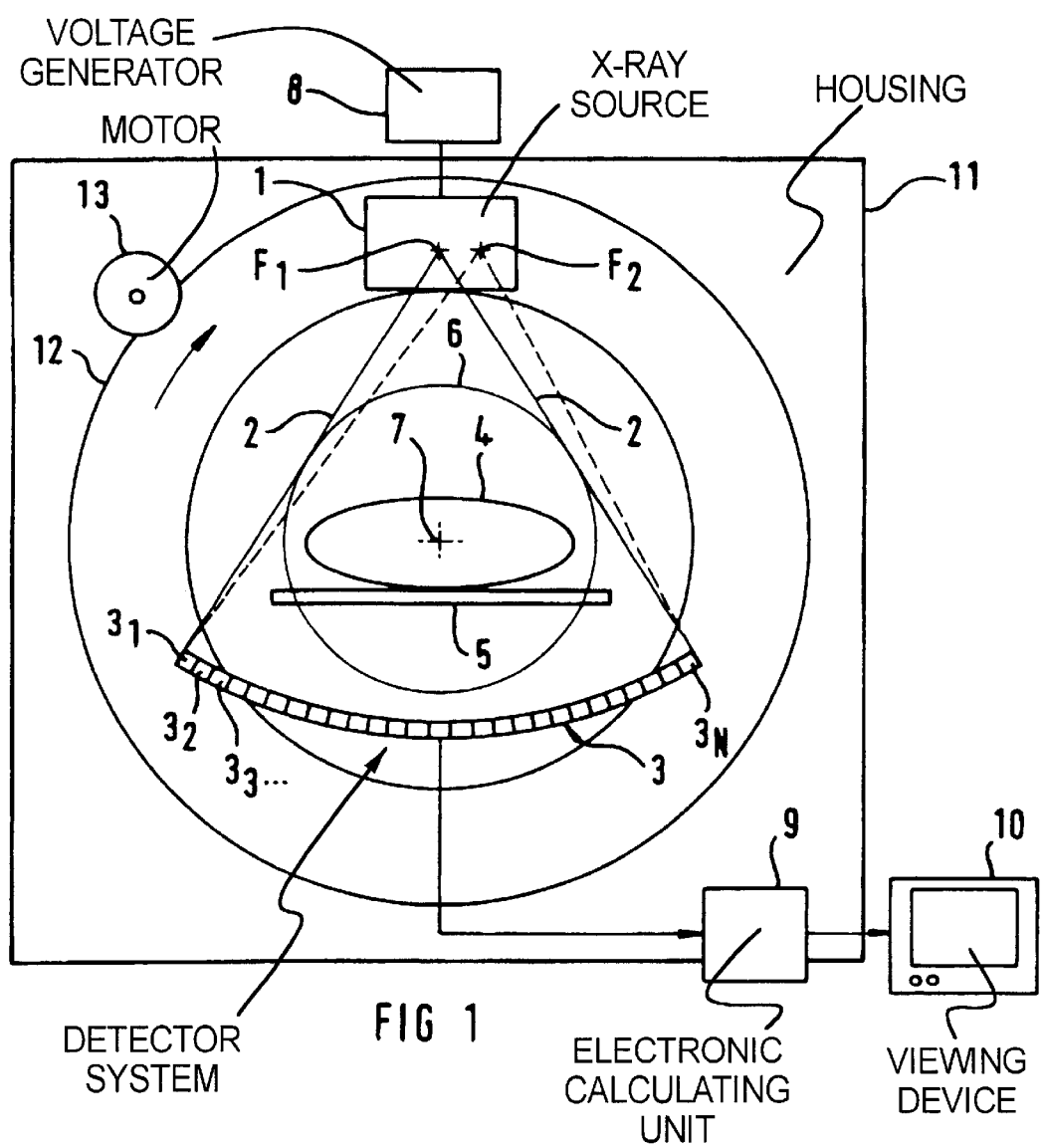
FIG. 1 is a block diagram of an inventive computer tomography apparatus.

The CT apparatus as illustrated in FIG. 1 has a measuring unit formed by an X-ray source 1 that emits a fan-shaped X-ray beam 2, and a detector system 3 that is constructed as a row of detector elements, for instance N=512 detector elements $3_1$ to $3_N$. A patient bed 5 is provided for patient 4, as the subject that is to be examined. For purposes of examining the patient 4, the measuring unit 1, 3 is rotated around a measuring field 6, in which the region of the patient 4 that is to be examined is located. The axis of rotation of the measuring unit 1, 3 is referenced 7. During the rotation, the X-ray source 1, which is supplied by a voltage generator 8, is pulsed or is driven with continuous radiation. At predetermined angle positions, for instance 360 angle positions at 1° intervals, sets of output data of the detector elements $3_1$ to $3_N$ of the detector system 3—known as projections—are generated.

In the case of the inventive CT apparatus, the focus of the X-radiation source 1 from which the X-rays emanate is moved back and forth periodically between two end positions, which are referenced F1 and F2 in FIG. 1. There is thus an alternating focus.

The corresponding output data are fed to an electronic computing unit 9, which computes a tomogram of the region of the patient 4 that is located in the measuring field 6 based on the output data fed to it. The tomogram is displayed on a viewing device 10.

The rotation of the measuring unit 1, 3 around the axis 7 is accomplished by means of a gantry 12 at which the X-ray source 1 and the detector system 3 are mounted. For driving the gantry 12, a motor 13 is provided, which is controlled by the electronic computing unit 9 in this case, as is the voltage generator 8. A separate control unit can be provided in addition to the electronic computing unit 9 instead. The gantry 12 and the motor 13 are mounted in a housing 11.

Figure 2:
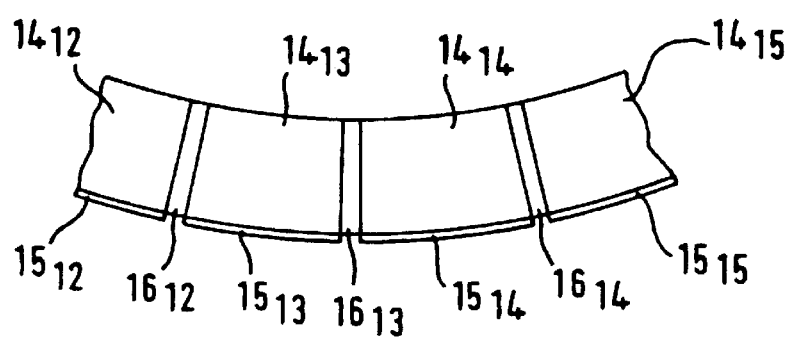
FIG. 2 is an enlarged view of a part of the detector system of the CT apparatus shown in FIG. 1.

As can be seen in FIG. 1 in combination with FIG. 2, the detector system 3 is composed of a row of detector elements $3_1$ to $3_N$, of which the detector elements $3_{12}$ to $3_{15}$ are illustrated in FIG. 2. Each detector element has a scintillation body—in FIG. 2, the scintillation bodies $14_{12}$ to $14_{15}$ —with a photoelectric converter connected downstream—in FIG. 2, photodiodes $15_{12}$ to $15_{15}$. The interspaces between immediately adjacent detector elements are respectively filled by a light-impermeable septum—the septa $16_{12}$ to $16_{14}$ are illustrated in FIG. 2—in order to prevent optical interference. Measured in the center plane of the fan-shaped X-ray beam 2, the individual detector elements respectively comprise the aperture ap. Also measured in the center plane of the X-ray beam 2, adjacent detector elements are arranged so as to be separated from one another by successive grid element spacings a.

In the inventive CT apparatus, given the use of a total of 512 detector elements, due to the alternating focus which moves between the two end positions in picking up a projection, there are 1024 of output data items available per projection, henceforth referred to as channels, which represent a fan projection of the region of the patient 4 that is to be examined. Thus, in a 360° revolution of the measuring unit 1, 2, 360 projections are picked up for every 1024 channels. The corresponding output data of the detector system 3 are supplied to the electronic computing unit 9, which processes the output data fed to it so that data are available corresponding to 360 parallel projections. The number of channels of the parallel projections, that is, the number of data items contained in one parallel projection, is greater than the number of channels of the output data corresponding to the fan projections. In this case, the number of channels of the parallel projections is greater than the number of channels of the output data by a factor which is at least equal to the ratio of the grid element spacing a to the aperture ap.

Based on these data corresponding to parallel projections, the electronic computing unit 9 reconstructs an image of the projected slice of the patient 4.

The conversion of the fan projections into parallel projections is accomplished in two steps in this case:

First, the fan projections are re-interpolated into parallel projections by interpolation in the azimuthal direction.

An interpolation in the radial direction then occurs, with the number of channels being increased as described above.

Assuming that the number of channels of the parallel projections is selected to corresponding to a factor which is equal to the ratio of the grid element spacing a to the aperture ap, a theoretical maximum scanning frequency results which is greater than the usual maximum scanning frequency that is theoretically achievable with an alternating focus by a factor a/ap, with the result that the theoretical maximum achievable spatial resolution is also increased by this factor, compared to the usual maximum spatial resolution that can be achieved in theory.

Assuming that a=0.114 cm for the grid element spacing and ap=0.097 cm for the aperture, there results a theoretical maximum scanning frequency for the inventive CT apparatus of $\rho_{max}$=2/0.097=20.6 1/cm, corresponding to a theoretical maximum spatial resolution of 1/0.097=10.3 lp/mm (line pairs per mm), compared to a theoretical maximum scanning frequency of only $\rho_0$=2/0.114=17.54 1/cm corresponding to a theoretical maximum spatial resolution of 1/0.114=8.77 lp/mm in the case of a conventional CT apparatus with an alternating focus. This corresponds to an increase of 18%.

Since 95% of the stated theoretical maximum achievable spatial resolution is attained in practice, one gets a maximum spatial resolution of 9.8 lp/cm is obtained.

The given values for the spatial resolution are values for high-contrast resolution, that is, contrast differences of approximately 1000 HU (Hounsfield Units).

In the case of the exemplary embodiment, the computing unit 9 executes the interpolation in the radial direction according to equation (1) above.

Figure 3:
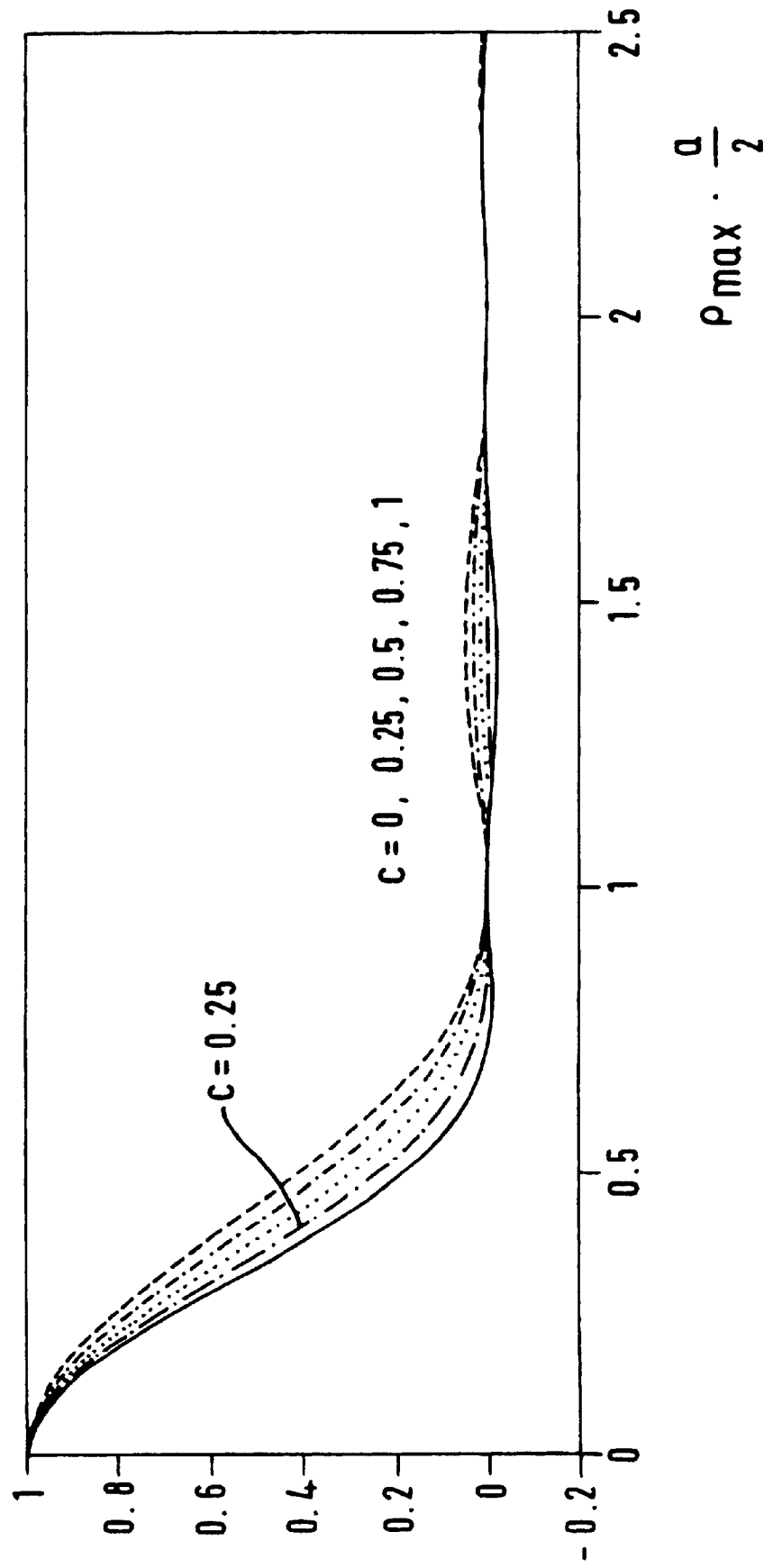
FIG. 3 shows curves for various Fourier-transform interpolation filters that can be used in the CT apparatus depicted in FIGS. 1 and 2.

The frequency response of this interpolation filter is illustrated in FIG. 3, whose frequency axis is normalized at $\rho^*$ a/2. It is clear from FIG. 3 that in order to avoid aliasing errors, a good smoothing around the original scanning frequency $\rho_0$=2/a is desirable, and the best suppression of frequencies above the maximum scanning frequency $\rho_{max}$ that exists subsequent to the re-interpolation is achieved in the case of the utilized interpolation filter, with a value of c=0.25 for the constant c.

When the image reconstruction data are loaded by the electronic computing unit 9 as described, the reconstruction of the image based on these data ensues, this being performed by the electronic computing unit 9 according to any suitable known method, for instance a Fourier method or a back projection method.

In the exemplary embodiment, a one-line detector system is provided, however, it is also possible to provide an inventive CT apparatus with a multi-line detector system. In such a case, the described procedure is followed for the output data delivered by each individual line of detectors.

If fewer than all the detector elements are used, for instance because the X-ray beam 2 is so gated for reducing the size of the measuring field, the number of detector elements actually used to pick up the projections of course should be used in the above-described procedure.

The described exemplary embodiment is a CT apparatus of the third generation, however, CT devices of the fourth generation can also be inventively constructed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography apparatus comprising:

an X-ray source having an alternating focus which is moved back and forth between two end positions;

means for rotating said X-ray source around an examination subject for irradiating said examination subject from a plurality of different projection angles;

a detector system, composed of a plurality of detector elements, for receiving X-rays from said alternating focus, attenuated by said examination subject, at each of said projection angles, each of said detector elements having an aperture and each of said detector elements being spaced by a grid element spacing from an adjacent detector element, said detector system emitting output data for each projection said output data comprising a number of output data items equal to twice the number of detector elements participating in obtaining the respective projection;

a computer, supplied with said output data, which converts said output data into image reconstruction data, said image reconstruction data containing a number of data items per projection which is greater than twice said number of detector elements participating in obtaining the projection, said computer reconstructing an image of said examination subject from said image reconstruction data and generating image signals representing said image; and a display, supplied with said image signals, for displaying said image.

2. A computed tomography apparatus as claimed in claim 1 wherein said computer converts said output data into said image reconstruction data to produce image reconstruction data containing a number of image reconstruction data items per projection which is greater than twice said number of detector elements participating in obtaining the respective projection by a factor which is at least equal to a ratio of said grid element spacing to said aperture.

3. A computed tomography apparatus as claimed in claim 1 wherein said X-ray source generates a fan beam and wherein said output data represent fan projections, and wherein said image reconstruction data represent parallel projections.

4. A computed tomography apparatus as claimed in claim 1 wherein said computer converts said output data into said image reconstruction data by interpolation of said output data.

5. A computed tomography apparatus as claimed in claim 4 wherein said computer interpolates said output data so that signal portions of said output data having a spatial frequency which is greater than or equal to a reciprocal of said spacing are substantially suppressed.

6. A computed tomography apparatus as claimed in claim 5 wherein said computer interpolates said output data according to the equation $$h_1^a(\beta,\Delta\beta) = ch_1(\beta,\Delta\beta) + (1-c)h_1^r(\beta,\Delta\beta)$$

wherein $h_1$ is the interpolation kernel of the linear interpolation, for which the equation $$h_1(\beta, \Delta\beta) = \begin{cases} 1 - \dfrac{|\beta|}{\Delta\beta} & |\beta| \le \Delta\beta \\ & \text{for} \\ 0 & \Delta\beta < |\beta| \end{cases} \qquad (2)$$

applies, wherein $h_1^r$ is defined by $$h_1^r(\beta, \Delta\beta) = \qquad (3)$$

$$\begin{cases} \dfrac{1}{3}\left(1 + \sqrt{1 - 3\left(\dfrac{\beta}{\Delta\beta}\right)^2}\right) & |\beta| \le 0.5\Delta\beta \\ \dfrac{1}{6}\left(2 + 3\left(1 - \left|\dfrac{\beta}{\Delta\beta}\right|\right) - \sqrt{1 - 3\left(1 - \left|\dfrac{\beta}{\Delta\beta}\right|\right)^2}\right) & \text{for } 0.5\Delta\beta < |\beta| \le 1.5\Delta\beta \\ 0 & 1.5\Delta\beta < |\beta| \end{cases}$$

and wherein $\beta$ is the fan channel angle and $\Delta\beta$ is its increment.

* * * * *